(12) United States Patent
Flach et al.

(10) Patent No.: US 10,780,194 B2
(45) Date of Patent: *Sep. 22, 2020

(54) MEDICAL DRESSING

(71) Applicant: Mölnlycke Health Care AB, Gothenburg (SE)

(72) Inventors: Niclas Flach, Alingsås (SE); Kristina Hamberg, Göteborg (SE); Ulf Johannison, Landvetter (SE); Bengt Söderström, Mölnlycke (SE)

(73) Assignee: Mölnlycke Health Care AB, Gothenburg (SE)

( * ) Notice: Subject to any disclaimer, the term of this patent is extended or adjusted under 35 U.S.C. 154(b) by 622 days.

This patent is subject to a terminal disclaimer.

(21) Appl. No.: 15/509,111

(22) PCT Filed: Sep. 9, 2015

(86) PCT No.: PCT/EP2015/070650
§ 371 (c)(1),
(2) Date: Mar. 6, 2017

(87) PCT Pub. No.: WO2016/038111
PCT Pub. Date: Mar. 17, 2016

(65) Prior Publication Data
US 2017/0258957 A1 Sep. 14, 2017

(30) Foreign Application Priority Data
Sep. 11, 2014 (EP) ..................... 14184436

(51) Int. Cl.
*A61F 13/00* (2006.01)
*A61L 15/44* (2006.01)
(Continued)

(52) U.S. Cl.
CPC ........ *A61L 15/58* (2013.01); *A61F 13/00063* (2013.01); *A61F 13/00991* (2013.01);
(Continued)

(58) Field of Classification Search
CPC ........... A61L 2300/104; A61L 26/0066; A61L 15/44; A61F 13/00063
(Continued)

(56) References Cited

U.S. PATENT DOCUMENTS

| 4,643,180 A | 2/1987 | Feld |
| 4,921,704 A | 5/1990 | Fabo |

(Continued)

FOREIGN PATENT DOCUMENTS

| CN | 1925819 A | 3/2007 |
| EP | 0255248 A2 | 2/1988 |

(Continued)

OTHER PUBLICATIONS

U.S. Appl. No. 15/509,029, filed Sep. 9, 2015, Niclas Flach.
(Continued)

*Primary Examiner* — Keri J Nelson
(74) *Attorney, Agent, or Firm* — Ballard Spahr LLP

(57) ABSTRACT

A medical dressing (30) is disclosed, comprising an adhesive layer (3) having a skin-facing surface (6) to adhere the medical dressing to a dermal surface, wherein said adhesive layer comprises a first chemical compound incorporated within said adhesive layer, and wherein at least a portion of said skin-facing surface comprises a coating (9) comprising a second chemical compound. Also disclosed is a method of manufacturing such a medical dressing.

15 Claims, 2 Drawing Sheets

(51) Int. Cl.
| | |
|---|---|
| *A61L 15/58* | (2006.01) |
| *A61F 13/02* | (2006.01) |
| *A61L 15/46* | (2006.01) |
| *A61L 15/26* | (2006.01) |
| *B05D 1/02* | (2006.01) |
| *B05D 3/02* | (2006.01) |
| *A61L 26/00* | (2006.01) |

(52) U.S. Cl.
CPC ...... *A61F 13/0206* (2013.01); *A61F 13/0213* (2013.01); *A61F 13/0246* (2013.01); *A61F 13/0253* (2013.01); *A61L 15/26* (2013.01); *A61L 15/44* (2013.01); *A61L 15/46* (2013.01); *B05D 1/02* (2013.01); *B05D 3/0254* (2013.01); *A61F 2013/0071* (2013.01); *A61F 2013/0074* (2013.01); *A61F 2013/0091* (2013.01); *A61F 2013/00519* (2013.01); *A61L 26/0066* (2013.01); *A61L 2300/104* (2013.01); *A61L 2300/202* (2013.01); *A61L 2300/206* (2013.01); *A61L 2300/208* (2013.01); *A61L 2300/404* (2013.01); *A61L 2420/02* (2013.01)

(58) Field of Classification Search
USPC .................. 602/48; 424/443, 445, 447–449
See application file for complete search history.

(56) References Cited

U.S. PATENT DOCUMENTS

| | | | |
|---|---|---|---|
| 2006/0141015 A1 | 6/2006 | Tessier et al. | |
| 2007/0203442 A1 | 8/2007 | Bechert et al. | |
| 2009/0104252 A1 | 4/2009 | Alam et al. | |
| 2012/0089068 A1 | 4/2012 | McClure, Jr. | |
| 2013/0101633 A1 | 4/2013 | Lowenhielm et al. | |
| 2013/0189339 A1* | 7/2013 | Vachon | A61K 31/167 424/404 |
| 2017/0258956 A1* | 9/2017 | Flach | A61L 15/26 |

FOREIGN PATENT DOCUMENTS

| | | |
|---|---|---|
| EP | 1960164 A1 | 8/2008 |
| EP | 1964580 A1 | 9/2008 |
| EP | 2837370 A1 | 2/2015 |
| JP | 2007517557 A | 7/2007 |
| WO | WO-97/042985 A1 | 11/1997 |
| WO | WO-2007/069990 A1 | 6/2007 |
| WO | WO-2008/057155 A1 | 5/2008 |
| WO | WO-2009/047564 A2 | 4/2009 |
| WO | WO-2011/007179 A1 | 1/2011 |
| WO | WO-2011/129759 A1 | 10/2011 |
| WO | WO-2013/128606 A1 | 9/2013 |
| WO | PCT/EP2015/070648 | 9/2015 |
| WO | WO-2016/038109 A1 | 3/2016 |

OTHER PUBLICATIONS

International Preliminary Report on Patentability dated Mar. 14, 2017 by the International Searching Authority for Application No. PCT/EP2015/070650, which was filed on Sep. 9, 2015 and published as WO/2016/038111 on Mar. 17, 2016 (Applicant—Mölnlycke Health Care AB // Inventors—Flach, et al.) (6 pages).

International Search Report and Written Opinion dated Nov. 12, 2015 by the International Searching Authority for Application No. PCT/EP2015/070648, which was filed on Sep. 9, 2015 and published as WO/2016/038109 on Mar. 17, 2016 (Applicant—Mölnlycke Health Care AB // Inventors—Flach, et al.) (11 pages).

International Preliminary Report on Patentability dated Mar. 14, 2017 by the International Searching Authority for Application No. PCT/EP2015/070648, which was filed on Sep. 9, 2015 and published as WO/2016/038109 on Mar. 17, 2016 (Applicant—Mölnlycke Health Care AB // Inventors—Flach, et al.) (8 pages).

International Search Report and Written Opinion dated Nov. 18, 2015 by the International Searching Authority for Application No. PCT/EP2015/070650, which was filed on Sep. 9, 2015 and published as WO/2016/038111 on Mar. 17, 2016 (Applicant—Mölnlycke Health Care AB // Inventors—Flach, et al.) (9 pages).

* cited by examiner

MEDICAL DRESSING

CROSS-REFERENCE TO RELATED APPLICATIONS

This application is a U.S. National Phase Application of International Application No. PCT/EP2015/070650, filed Sep. 9, 2015, which claims priority to European Application No. 14184436.5, filed Sep. 11, 2014, each of which are hereby incorporated by reference in their entirety.

FIELD OF INVENTION

The present invention relates to a medical dressing.

BACKGROUND OF THE INVENTION

A wound caused by an injury or disease may be treated by the use of a bandage or wound dressing to promote healing by preventing infection and leakage from the wound. Many known wound dressings include a self-adhering adhesive, also known as pressure-sensitive adhesive (PSA), which purpose is to adhere to the wound and/or to the skin surrounding the wound and thus to fixate the dressing in a desirable position. Various adhesives are being used for affixing medical products on the skin, some of the most common being encompassed by the terms acrylic adhesives, silicone based adhesives and hot melt adhesives, among others.

In order to ensure that a medical device such as a wound dressing remains in the same position after a certain time of use, an adhesive having a strong adherence, e.g. an acrylic adhesive, may be used. However, in case the medical device is to be attached directly on the skin, an acrylic based adhesive increases the risk for pain and damages to the skin when such medical device is to be removed from the skin, e.g. due to skin stripping.

In contrast to acrylic adhesives, silicone based adhesives are known in the art to be very gentle on the skin. This is because a silicone based adhesive is typically relatively soft and therefore it can follow the contours of the skin well, resulting in a large contact surface area between the adhesive and the skin. Thus, although the actual adhesive force in each contact point of a silicone based adhesive is less than that of an acrylic adhesive, the large contact surface area achieved with a silicone based adhesive affords a high overall adherence to the skin, whilst at the same time being skin-friendly, i.e. when a silicone based adhesive is removed from the skin very few skin cells are removed due to the low adhesive force in each contact point, thereby the above mentioned problem of skin stripping can be avoided.

For some type of wounds, such as for example severe burns and chronic wounds, there is a particular need to use a wound dressing that includes an antimicrobial agent to thereby eliminate or reduce the risk of infection of the wound. To that end, various types of antimicrobial dressings have been developed. Examples of antimicrobial agents that have been explored for use in wound dressings include conventional antiseptics, antibiotics, antimicrobial peptides, or metallic agents with antimicrobial properties. For example, silver-containing compounds, such as silver salts, are commonly used in antimicrobial wound dressings.

WO2008057155 discloses silicone gel forming compositions for temporarily adhering a medical device to a biological substrate, such as skin. Said disclosure teaches silicone gel compositions comprising active agents, for instance antibiotics, antiseptics, antifungals, anti-inflammatory agents, hormones, anticancer agents, histamine blockers, beta blockers, vitamins, sedatives, analgesics, proteolytic enzymes, and peptides, which can be bound in the composition. However, the release of the active agent from the hydrophobic adhesive matrix, i.e. the silicone gel forming composition, is typically limited as active agents are bound in the composition.

WO 2011/129759 discloses an antimicrobial silicone gel adhesive (and wound dressing including a layer of such silicone gel adhesive) comprising at least one silver salt and at least one hydrophilic component, wherein the hydrophilic component facilitates the absorbance of moisture in the adhesive layer and thereby affording an improved release of silver from the adhesive matrix.

However, there is still a need in the art to provide an improved adherent medical dressing.

SUMMARY OF THE INVENTION

In view of the above-mentioned and other drawbacks of the prior art, a general object of the present invention is to provide an adherent medical dressing, in particular to provide an adherent medical dressing capable of achieving an instant and sustained release of a chemical compound, such as an antimicrobial compound, whilst maintaining a presence of a chemical compound in the dressing.

According to a first aspect of the invention, these and other objects are achieved through a medical dressing comprising an adhesive layer having a skin-facing surface to adhere the medical dressing to a dermal surface, wherein the adhesive layer comprises a first chemical compound incorporated within said adhesive layer, and wherein at least a portion of the skin-facing surface comprises a coating comprising a second chemical compound.

The invention is based on the realization that an improved release of active chemical compound(s) and/or an improved biological activity (e.g. antimicrobial and/or wound healing activity) from an adherent medical dressing can be achieved by an adhesive layer having a skin-facing surface comprising a coating comprising a second chemical compound, which coating is intended to be in direct contact with a wound and/or surrounding dermal surface during use, wherein the adhesive layer comprises a first chemical compound incorporated within the adhesive layer. Thereby, the coating on the adhesive layer provides a rapid initial release of the second chemical compound, whilst a more slow release of the first chemical compound from the adhesive layer is provided, to thereby ensure that the release thereof is maintained over a desirable period of time and/or that a biological (e.g. antimicrobial) activity therefrom is maintained over a desirable period of time.

In embodiments of the invention, the first chemical compound may be a solid dispersion within the adhesive layer. For example, the first chemical compound may be a plurality of solid particles distributed within the adhesive layer.

In embodiments of the invention, the first chemical compound may be a molecular dispersion or partial molecular dispersion within the adhesive layer.

By "molecular dispersion" should be understood isolated molecules of the chemical compound, and by "partial molecular dispersion" should be understood a plurality of isolated molecules as well as a plurality of isolated clusters of molecules e.g. crystals or particles.

In embodiments of the invention, the adhesive layer may comprise a silicone based adhesive. The inventors have realized that a silicone based adhesive is particularly suitable as chemical compounds can be included in a coating thereon without substantially affecting the adhesive properties of the adhesive layer whilst the chemical compounds can be readily released therefrom.

The term "coating" should, in the context of this application, be understood as at least one continuous layer on a surface, or a plurality of dots or layers, or a discontinuous cover on a surface e.g. plurality of particles distributed on an area of a surface.

In embodiments of the invention, the coating comprising the second chemical compound on at least a portion of the skin-facing surface of the adhesive layer may comprise a plurality of particles of the second chemical compound distributed on at least a portion of the skin-facing surface, wherein a first portion of each particle may penetrate into the adhesive layer whilst a second portion of the particle may protrude out from the adhesive layer.

In embodiments of the invention, the coating comprising the second chemical compound is intended to be in direct contact with a wound and/or surrounding dermal surface, during use of the medical dressing.

In embodiments of the invention, the coating comprising the second chemical compound on the adhesive layer may, for example, be a film coating comprising a composition including the second chemical compound and a film forming or carrier chemical compound (e.g. a polymeric compound).

In embodiments of the invention, the medical dressing may further comprise a substrate having a first surface facing the adhesive layer, wherein the skin-facing surface of the adhesive layer faces away from said first surface of said substrate.

In embodiments of the invention, the adhesive layer may be a coating on at least a portion of said first surface of the substrate, thereby facilitating the application of the substrate of the medical dressing to desired position, for example, such that the substrate adheres to and covers a wound. By providing a coating comprising a second chemical compound, such as for example an antimicrobial compound or wound healing compound, on the skin-facing surface of the adhesive layer, the release of the second chemical compound can be controlled and restricted to a desired application area.

In embodiments of the invention, the medical dressing may further comprise a perforated film layer sandwiched between the first surface of the substrate and the adhesive layer, wherein the adhesive layer may be a coating on a non-perforated portion of the perforated film layer. For example, a top surface of a perforated film layer may be attached to first surface of the substrate, wherein the adhesive layer may be coated on a bottom surface of a portion of the perforated film, and wherein the top surface of the perforated film layer is opposite to, or faces away from, the bottom surface thereof. The perforated film layer may, for example, be a perforated polymeric film layer such as a perforated polyurethane film layer having a thickness of for example 10 to 150 μm.

Accordingly, the first surface of the substrate may be exposed through the openings of the perforated film layer, thereby facilitating the absorption of exudate and wound fluids from the wound, and/or facilitating the release of the first chemical compound from the substrate to the wound, through the openings.

By the term "attached" as used herein should be understood one physical element being in contact with another physical element, e.g. a first layer being in contact with an adjacent second layer. For example, in embodiments of the invention, the term "attached" may mean that one layer is adhered or laminated to another layer by means of an adhesive in between the attached layers, alternatively two layers may be "attached" without direct adhesive means therebetween, for example, one layer may be placed on top of another layer wherein the layers are held together by additional surrounding layers enclosing the "attached" layers.

In embodiments of the invention, the substrate may comprise an absorbent material. For example, in embodiments of the invention, the absorbent material may be selected from the group consisting of polymeric foam such as a hydrophilic polyurethane foam, a non-woven material, fibrous material such as fibrous hydrophilic polymeric material, gel forming fibers, hydrogel, a matrix containing hydrocolloids, woven and knitted fibers. Thereby, the medical dressing is capable of absorbing and retaining exudates from a wound.

As used herein, the term "hydrophilic" refers to the water-permeability property of a material or the water-attracting property of a molecule. In the context of a material with pores (such as, for example, open-cell foams) or materials with through-holes, such a material is "hydrophilic" if the material wicks up water. In the context of a material without pores or any through-holes, such a material is considered "hydrophilic" if it does not resist the flow of water into or through the material. For example, hydrophilicity of a material can be tested using a water column of up to one inch height exerting pressure on the material for at least 60 minutes, at least 90 minutes, or at least 24 hours. By "resisting," it is meant that any flow of water into or through the foam in such a test is below a detection limit for the test.

In embodiments of the invention, the substrate may comprise a layer of hydrophilic polyurethane foam material. For example, the hydrophilic foam may be an open-cell porous foam such an hydrophilic polyurethane foam. The foam may for example be a polyurethane foam produced from a composition comprising a prepolymer based on: hexamethylene diisocyante (HDI), toluene diisocyanate (TDI), or methylene diphenyl diisocyanate (MDI).

In embodiments of the invention, the substrate may be polymeric film, such as a polyurethane film. For example, the substrate may be a polyurethane film having a thickness of 10 to 150 μm, such as 10 to 100 μm or 10 to 50 μm.

In embodiments of the invention, the substrate may be perforated polymeric film, for example a perforated polyurethane film having a thickness of 10 to 150 μm, such as 10 to 100 μm or 10 to 50 μm, wherein the adhesive layer may be a coating on a non-perforated portion thereof.

In embodiments of the invention, the substrate may be a net-like porous reinforcing layer as, for example, disclosed in U.S. Pat. No. 4,921,704, wherein the reinforcing layer is substantially completely encapsulated by the adhesive layer. The reinforcing layer may for example be a flexible and elastically-extendible net of textile material, for example a polyamide net.

In embodiments of the invention, the first chemical compound and/or the second chemical compound may be an antimicrobial compound.

In embodiments of the invention, the first chemical compound and the second chemical compound may independently be selected from the group consisting of a silver compound such as silver salt and metallic silver, biguanide salts such as polyhexamethylene biguanide (PHMB) or any salts thereof, or polyhexamethyl guanide (PHMG) or any salts thereof, or chlorhexidine or any salts thereof, iodine, salicylic acid or any salt thereof, acetylsalicylic acid or any salt thereof, quarter ammonium salts such as benzethonium chloride, povidone-iodine (betadine), lactoferrin, xylitol, antimicrobial peptides such as human cationic antimicrobial protein 18 (hCAP18 or LL37), borneol, bismuth subgallate, antifungal pharmaceuticals, and antibiotics such as gentamycin, streptomycin.

In embodiments of the invention, the first chemical compound and the second chemical compound may independently be selected from the group consisting of a silver compound including e.g. a silver salt and metallic silver; biguanide salts such as PHMB or any salts thereof, or PHMG or any salts thereof; chlorhexidine or any salts thereof; and iodine.

For example, the first chemical compound and/or the second chemical compound may be a silver salt such as silver sulfate ($Ag_2SO_4$), silver sulfite ($Ag_2SO_3$), silver nitrate ($AgNO_3$), silver carbonate ($AgCO_3$), silver phosphate ($Ag_3PO_4$), silver chloride (AgCl), silver sodium hydrogen zirconium phosphate (AlphaSan® from Milliken Chemical, Spartanburg, USA), or PHMB e.g. PHMB hydrochloride or any other salts thereof, or chlorhexidine or any salts thereof.

For example, the first chemical compound and/or the second chemical compound may be a silver compound, for example a silver salt or metallic silver.

In embodiments of the invention, the first chemical compound may be present in a first concentration by area of the medical dressing and the second chemical compound may be present in a second concentration by area of the medical dressing, wherein the first and second concentrations may be different.

By varying the concentrations of the first and second chemical compounds, the release profile of the dressing can be tailor made for different applications; i.e. different types of wounds.

In embodiments of the invention, the concentration of the first chemical compound may be about 5 to 3000 $\mu g/cm^2$, and wherein the concentration of the second chemical compound may be about 1 to 2500 $\mu g/cm^2$. For example, the concentration of the first chemical compound may be about 5 to 3000 $\mu g/cm^2$, and wherein the concentration of the second chemical compound may be about 1 to 2500 $\mu g/cm^2$.

As used herein, the terms "about" or "approximately," refer to, for example, a number or percentage, generally including numbers that fall within a range of 5%, 10%, or 20% in either direction (plus or minus) of the number unless otherwise stated or otherwise evident from the context (except where such a number would be physically impossible, e.g. exceed 100% of a possible value or fall below 0% of a possible value).

In embodiments of the invention, the adhesive layer may further comprise a hydrophilic component, as for example disclosed in WO 2011/129759, hereby incorporated by reference. Thereby, the release of the first chemical compound from the adhesive layer may be adapted. Examples of such hydrophilic component include, but are not limited to, mono- di- and/or polysaccharides, sugar alcohols, polyols, polyethers, polyesters, polyamides, and/or polymers comprising pendant carboxylic acid groups and/or pendant sulphonate groups.

In embodiments of the invention, the substrate may comprise a third chemical compound, wherein the third chemical compound may be same as the first and/or second chemical compound.

In embodiments of the invention, the third chemical compound may be a solid dispersion in the substrate. The third chemical compound may be a substantially homogenous solid dispersion in the substrate. For example, the third chemical compound may be a molecular dispersion or partial molecular dispersion in the substrate.

In embodiments of the invention, the substrate may be impregnated with the third chemical compound. For example, the substrate may be a foam having an open cell structure, wherein the third chemical compound may be present as a coating on the cell walls of the foam. For example, the substrate may be soaked with a solution or dispersion containing the third chemical compound.

In embodiments of the invention, the substrate may include a plurality of layers of the same or different materials. For example, the substrate may comprise a wound facing layer of absorbent foam material, a middle fibrous gel forming layer, and a top non-woven layer, wherein the middle layer may be sandwiched between the wound facing layer and the top layer. Thereby the liquid absorption properties of the medical dressing may be adapted as desired. Further, the third chemical compound may be incorporated with all or only selected layer of the substrate to achieve a desirable release from and/or activity within the substrate.

In embodiments of the invention, the medical dressing may include a vapor permeable transmission layer attached to the substrate on a second surface thereof, the second surface being opposite to the first surface of the substrate. The transmission layer may typically be water impermeable.

According to a second aspect of the invention, the above-mentioned and other objects are achieved by a method of manufacturing a medical dressing comprising the steps of:
  providing an adhesive layer comprising a first chemical compound; and
  providing a coating comprising a second chemical compound on said adhesive layer.

According to a third aspect of the invention, the above-mentioned and other objects are achieved through a medical dressing manufactured according to the above-described method.

According to a forth aspect of the invention, the above-mentioned and other objects are achieved through the use of the medical dressing according to the invention for treating and/or preventing wounds. For example, the medical dressing according to the invention may be used in the treatment of burns, scars, bacterial infections, viral infections, fungal infection, and/or for wound healing.

According to a fifth aspect of the invention, the above-mentioned and other objects are achieved through a method of treating a wound comprising the step of providing the medical dressing according to the invention on a wound and/or surrounding dermal surface.

BRIEF DESCRIPTION OF THE DRAWINGS

These and other aspects of the invention will now be shown in more detail, with reference to the appended drawings showing an exemplary embodiment of the invention, wherein:

FIG. 1b is an enlarged cross-sectional view of the cut out X in FIG. 1a.

DESCRIPTION OF EXAMPLE EMBODIMENTS OF THE INVENTION

In the following description, example embodiments of the present invention are described with reference to the accompanying schematic drawings.

Figure 1A:
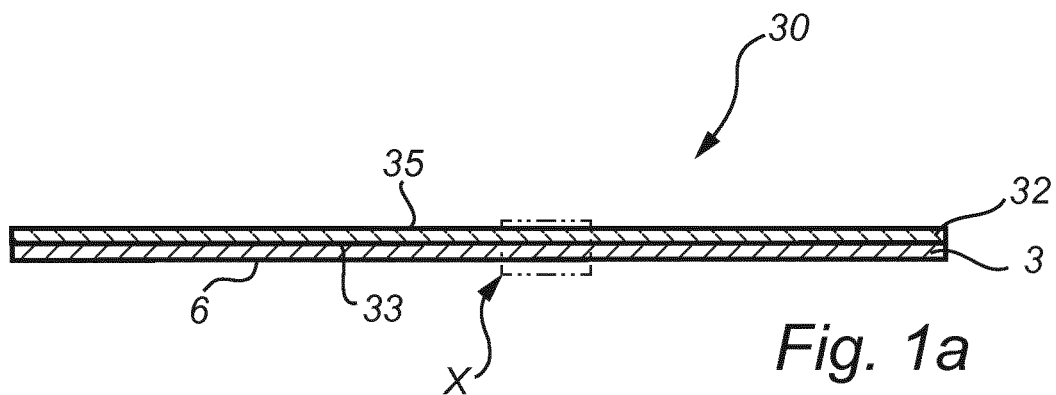
FIG. 1a is a cross-sectional view of an embodiment of a medical dressing according to the invention.

FIG. 1a shows an embodiment of a medical dressing 30 according to the invention, wherein the medical dressing 30 comprises an adhesive layer 3 having a skin-facing surface 6 to adhere the medical dressing to a dermal surface, wherein the adhesive layer 3 comprises a first chemical compound distributed within the adhesive layer 3, and wherein at least a portion of the skin-facing surface 6 comprises a coating 9 comprising a second chemical compound.

Thereby, the coating 9 on the adhesive layer provides a rapid initial release of the second chemical compound, whilst a more slow release of the first chemical compound from within the adhesive layer is provided to thereby ensure that the release of the first chemical compound is maintained over a desirable period of time and/or that a biological (e.g. antimicrobial) activity exhibited by the first chemical compound is maintained over a desirable period of time.

Different types of wounds pose different demands on a dressing. For application on deep wounds, resulting from e.g. surgery, it may be advantageous to provide a more prominent initial release of the second chemical compound to facilitate early healing and avoid swelling at the wound site. For the purposes of infection prevention or remediation of scars, a slower release may be desired.

By varying the concentrations of the first and second chemical compounds, the release profile of the dressing can be tailor made for different applications. This allows for a more controlled release of the first and second chemical compounds.

Figures 2A, 2B, 2C:
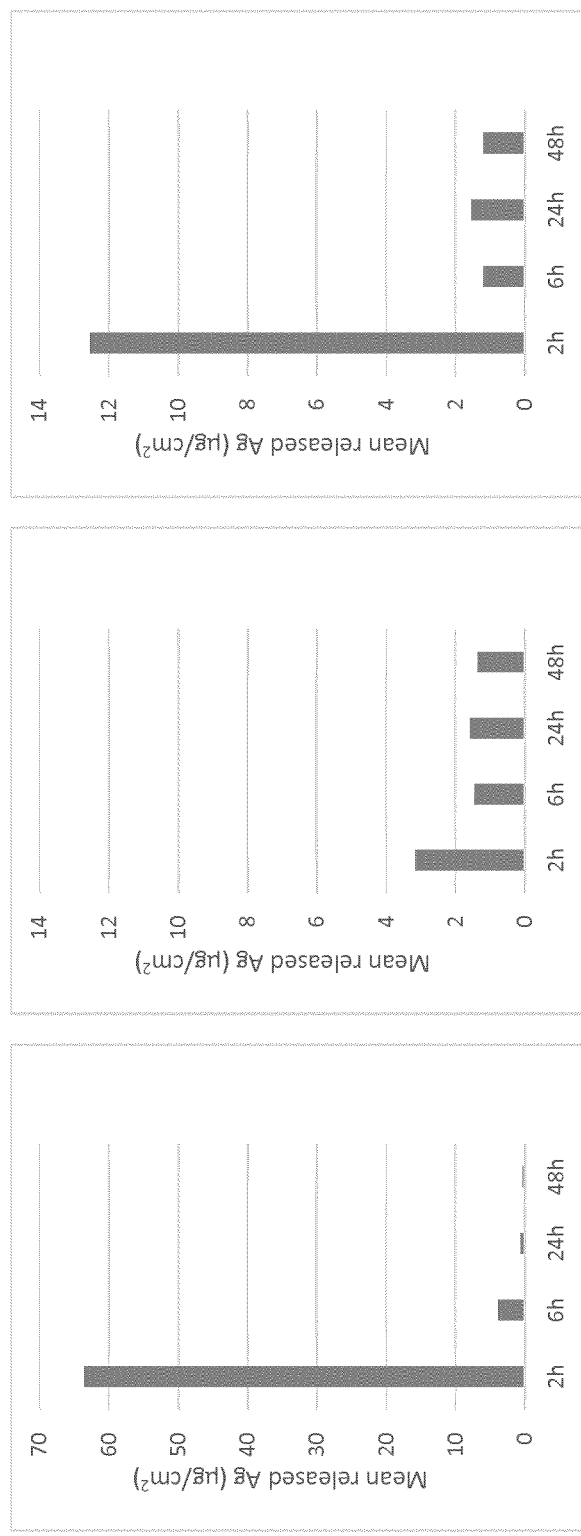
FIG. 2 illustrates the released amount of silver over time for a dressing according to the present invention compared to prior art dressings.

As illustrated in FIG. 2, a dressing comprising only the second chemical compound on the surface provides for an excessive and quick release (FIG. 2a); i.e. a strong (e.g. antimicrobial) effect initially, but the dressing material becomes depleted of the chemical compound quickly. This is not advantageous, since such a dressing would need to be changed often. There may also be a risk of uncontrolled and disproportionate release, which may cause toxicity at the wound site.

In contrast, a dressing comprising only the first chemical compound in the adhesive layer (FIG. 2b) lacks an initial effect, but a stable release at a lower level is achieved. The chemical compound incorporated in the adhesive layer is less accessible, and cannot exert the effect as rapidly or efficiently.

A dressing according to the invention allows for a synergistic effect by providing a rapid initial release of the second chemical compound, whilst a more slow release of the first chemical compound from within the adhesive layer (FIG. 2c). This allows for a more controlled release profile, and thereby a strong initial, efficient as well as sustained effect.

As exemplified in FIG. 1a, the medical dressing 30 may further include a substrate 32, wherein the adhesive layer 3 may be coated on a first surface 33 of the substrate 32, which may, for example as depicted in FIG. 1, be a plastic film such as a polyurethane film. For example, the substrate 32 may be a polyurethane film having a thickness in the range of from 10 to 150 μm, such as from 10 to 100 μm or from 10 to 80 μm, or from 10 to 50 μm. Alternatively, the substrate 32 may be a perforated plastic film which may comprise a plurality of openings (or through holes) (not shown in FIG. 1a) of any desirable size and shape, wherein the adhesive layer is a coating on the non-perforated portions of the perforated film. The shape and size of the openings in the perforated film may advantageously be adapted to achieve a desirable transport of liquid through the perforated film, e.g. transport of wound fluids to a proximal absorbent member of the medical dressing or separate dressing (not shown in FIG. 1a). For example, the shape and size of the openings in the perforated film may be adapted to achieve a desirable breathability e.g. as determined by water vapor transmission rate.

In embodiments of the invention, the first chemical compound may be a solid dispersion within the adhesive layer. For example, the first chemical compound may be a plurality of solid particles distributed within the adhesive layer.

In embodiments of the invention, the first chemical compound may be a molecular dispersion or partial molecular dispersion within the adhesive layer.

For example, the first chemical compound may be substantially homogenously mixed within matrix of the adhesive layer. For example, the first chemical compound, in particle form or as liquid solution or suspension, may be added to a (non-cured) adhesive mixture which is subsequently coated on a substrate and thereafter cured.

In embodiment of the invention, the adhesive layer may further comprise an hydrophilic component which may enhance the water permeability and/or water absorption capacity of the adhesive layer, and thereby the release of the first chemical compound from the adhesive layer may be further adapted. Examples of such hydrophilic component include, but are not limited to, mono- di- and/or polysaccharides, sugar alcohols, polyols, polyethers, polyesters, polyamides, and/or polymers comprising pendant carboxylic acid groups and/or pendant sulphonate groups. For example, the hydrophilic component may be a carboxymethyl cellulose (CMC), polyvinyl alcohol (PVA) or a polyethylene glycol (PEG)

In embodiments of the invention, the medical dressing 30 may also further include a vapor permeable transmission layer (not shown in FIG. 1a) that overlays a second surface 35 of the substrate 32. The permeable transmission layer may be a plastic film, for example, comprising or consisting of polyurethane, polyethylene, or polypropylene. The vapor permeable transmission layer may be a polyurethane film having a thickness in the range of 10-100 μm, for example, 10-80 μm such as 10-50 μm.

In embodiments of the invention, the adhesive layer may be a standalone adhesive sheet (not shown) which may comprise a reinforcement layer, such as a perforated plastic film or fiber net (e.g. polyamide net), that is incorporated within the adhesive sheet to improve inter alia cohesion thereof. The adhesive layer 3 in FIG. 1 may for example comprise a silicone based adhesive.

In embodiments of the invention, the substrate 32 may comprise an absorbent material. For example, such absorbent material may be selected from the group consisting of a polymeric foam such as a hydrophilic polyurethane foam, a non-woven material, fibrous material such as fibrous hydrophilic polymeric material, gel forming fibers, hydrogel, a matrix containing hydrocolloids, woven and knitted fibers.

In embodiments of the invention, the substrate 32 may comprise a layer of a hydrophilic polyurethane foam, for example, a polyurethane foam produced from a composition comprising a prepolymer based on: hexamethylene diisocyante (HDI), toluene diisocyanate (TDI), or methylene diphenyl diisocyanate (MDI).

For example, in embodiments of the invention, the substrate 2 may be a hydrophilic polyurethane foam.

In embodiments of the invention, the coating comprising the second chemical compound may be in the form of particles (e.g. crystals or precipitate) wherein at least a portion of each particle 9 penetrates into the adhesive layer 3, whilst a second portion of the particle protrudes up from the adhesive layer 3 above the skin-facing surface 6 thereof. Thus, as the coating comprising the second chemical compound is on and/or protruding up from the adhesive layer 3, the release of the second chemical compound from the skin-facing surface 6 of the adhesive layer 3 is facilitated.

Figure 1B:
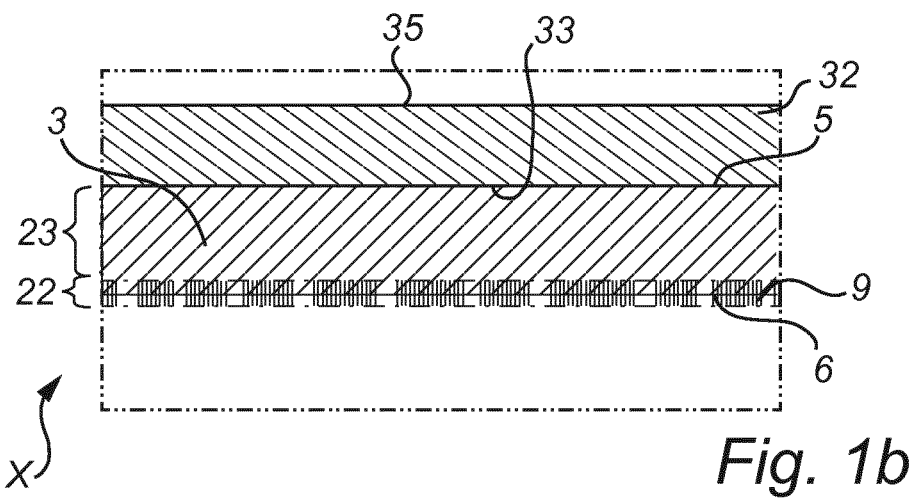

In embodiments of the invention, as illustrated in FIG. 1b, the adhesive layer 3 may comprise a skin portion 22 including the adhesive material of the adhesive layer 3 proximal to the skin-facing surface 6, and a non-skin portion 23 including the adhesive material proximal to the non-skin facing surface 5 of the adhesive layer 3 being opposite to the skin-facing surface 6, wherein the substrate portion 23 is substantially free from the second chemical compound.

In embodiments of the invention, the coating 9 comprising the second chemical compound on the skin-facing surface 6 of the adhesive layer 3 may be a film coating further comprising a film forming or carrier chemical compound such as, for example, polyvinylpyrrolidone (PVP), carboxymethyl cellulose (CMC), hydroxyethyl cellulose (HEC), polyvinyl alcohol (PVA) and/or hydroxypropyl cellulose (HPC). For example, in such film coating the second chemical compound may be enclosed in a matrix of the film forming or carrier chemical compound. Thereby, the release of the second chemical compound may be further controlled by selecting a film forming or carrier chemical compound having desirable properties, that is, by selecting for example a film forming or carrier chemical compound that has more or less solubility in an aqueous solution (e.g. wound fluid) the release of the second chemical can be adapted as desired.

In embodiments of the invention, the adhesive layer 3 may comprise a silicone based adhesive, acrylic adhesive, or a pressure-sensitive adhesive (PSA) holtmelt.

In embodiments of the invention, the adhesive layer 3 may be a coating having a coating weight of from 20 to 300 g/m$^2$, for example from 50 to 200 g/m$^2$ such as from 80 to 150 g/m$^2$.

In embodiments of the invention, the adhesive layer 3 may be a silicone based adhesive. For example, the silicone based adhesive may be a soft silicone gel adhesive which adhesive is known for its advantageous skin friendly properties as inter alia no or little skin is stripped off when an adhesive layer of soft silicone gel adhesive is removed from a dermal surface. The term "silicone gel" refers to a silicone gel that comprises a cross-linked network including silicone of lower molecular weight. For example, suitable soft silicone gel adhesives can be composed of an addition-cured RTV (Room Temperature Vulcanizing) silicone system which, after admixture, crosslinks and forms a self-adhesive elastomer. One example of a commercially available RTV addition-cured silicone system is Wacker SilGel 612 which is a two-component system, wherein the softness and degree of adherence of the formed elastomer can be varied by varying the proportions of the two components A:B from 1.0:0.7 to 1.0:1.3. Other examples of silicone based adhesives include inter alfa NuSil MED-6340, NuSil MED3-6300 and NuSil MED 12-6300 from NuSil Technology, Carpinteria, Ga., USA, and Dow Corning 7-9800 from Dow Corning Corporation, Midland, USA.

In embodiments of the invention, the first chemical compound and the second chemical compound may independently be selected from the group consisting of a silver compound including e.g. a silver salt and metallic silver, biguanide salts such as polyhexamethylene biguanide (PHMB) or any salts thereof, or polyhexamethyl guanide (PHMG) or any salts thereof, or chlorhexidine or any salts thereof, iodine, salicylic acid or any salt thereof, acetylsalicylic acid or any salt thereof, quarter ammonium salts such as benzethonium chloride, povidone-iodine (betadine), lactoferrin, xylitol, antimicrobial peptides such as human cationic antimicrobial protein 18 (also known as hCAP18 or LL37), borneol, bismuth subgallate, antifungal pharmaceuticals, and antibiotics such as gentamycin, streptomycin.

In embodiments of the invention, the first chemical compound and the second chemical compound may independently be selected from the group consisting of a silver compound including e.g. a silver salt and metallic silver; PHMB or any salts thereof; PHMG or any salts thereof; chlorhexidine or any salts thereof; and iodine.

For example, the first chemical compound and/or the second chemical compound may be a silver salt such as silver sulfate ($Ag_2SO_4$), silver sulfite ($Ag_2SO_3$), silver nitrate ($AgNO_3$), silver carbonate ($AgCO_3$), silver phosphate ($Ag_3PO_4$), silver chloride ($AgCl$), silver sodium hydrogen zirconium phosphate (AlphaSan® from Milliken Chemical, Spartanburg, USA), or PHMB e.g. PHMB hydrochloride or any other salts thereof, or chlorhexidine or any salts thereof.

For example, in embodiments of the invention, the first chemical compound may be a silver compound e.g. silver salt or metallic silver, wherein the second chemical compound may be PHMB or any salts thereof. Alternatively, the first chemical compound may be PHMB or any salt thereof and second compound may be a silver compound or both the first and second may be PHMB or any salt thereof, or both the first and second may be a silver compound. Alternatively, chlorhexidine or any salts thereof may be combined with a silver compound.

In embodiments of the invention, the first chemical compound may be present in a first concentration by area of the medical dressing and the second chemical compound may be present in a second concentration by area of the medical dressing, wherein the first and second concentrations are different. For example, the first concentration may typically be higher than the second concentration.

In embodiments of the invention, the concentration of the first chemical compound may be about 5 to 3000 μg/cm$^2$, and wherein the concentration of the second chemical compound may be about 1 to 2500 μg/cm$^2$. For example, the concentration of the first chemical compound may be about 50 to 2000 μg/cm$^2$, and wherein the concentration of the second chemical compound may be about 1 to 150 μg/cm$^2$. For example, the concentration of the first chemical compound may be about 1000 to 2500 μg/cm$^2$, and wherein the concentration of the second chemical compound may be about 1 to 300 μg/cm$^2$. For example, the concentration of the first chemical compound may be about 1500 to 2000 μg/cm$^2$, and wherein the concentration of the second chemical compound may be about 1 to 100 μg/cm$^2$. For example, the concentration of the first chemical compound may be about 50 to 200 μg/cm$^2$ such as 95 μg/cm$^2$, and wherein the concentration of the second chemical compound may be about 5 to 49 μg/cm$^2$ such as 20 μg/cm$^2$.

For most wound care applications, it is desirable to incorporate a larger amount of the first chemical compound into the adhesive layer, and a smaller amount of the second chemical compound in the surface coating.

For example, the ratio between the second and the first concentration may be in the range of 1:5 to 1:100, e.g. 1:10 to 1:50.

This allows for both a strong initial, and sustained effect of the first and second chemical compounds. The release of the first and second chemical compounds can be maintained over a desirable period of time and the biological activity of the chemical compounds can be maintained over a desirable period of time.

In embodiments of the invention, the first chemical compound and/or the second chemical compound may be a wound healing compound, wherein the first chemical compound and/or the second chemical compound may independently be selected from the group consisting of Edaravone (3-methyl-1-phenyl-2-pyrazolin-5-one); full protein or peptides of: amelogenin, fibronectin, vitronectin, fibrinogen; arginylglycylaspartic acid (RGD) peptides; betaglucan (BG) (e.g. soluble BG or oat BG), growth factors such as platelet-derived growth factor (PDGF), epidermal growth factor (EGF), fibroblast growth factor (FGF); cytokines such as transforming growth factor (TGF) beta 1, TGF beta 3, interleukin (IL)-10; decellularized animal tissue; and amniotic tissue.

In embodiments of the invention, the first chemical compound may be an antimicrobial compound selected from the group consisting of silver compound including e.g. a silver salt and metallic silver; PHMB or any salts thereof; PHMG or any salts thereof, chlorhexidine or any salts thereof; and iodine, wherein the second chemical compound may be a wound healing compound selected from the group consisting of Edaravone (3-methyl-1-phenyl-2-pyrazolin-5-one); full protein or peptides of: amelogenin, fibronectin, vitronectin, fibrinogen; arginylglycylaspartic acid (RGD) peptides; betaglucan (BG) (e.g. soluble BG or oat BG), growth factors such as platelet-derived growth factor (PDGF), epidermal growth factor (EGF), fibroblast growth factor (FGF); cytokines such as transforming growth factor (TGF) beta 1, TGF beta 3, interleukin (IL)-10; decellularized animal tissue; and amniotic tissue.

In embodiments of the invention, the substrate may comprise a third chemical compound, wherein the third chemical compound may be same as the first and/or second chemical compound.

In embodiments of the invention, the third chemical compound may be distributed within the substrate. For example, the third chemical compound may be substantially homogenously distributed within the substrate, i.e. having a uniform material composition throughout the substrate. For example, the third chemical compound may be a substantially homogenous solid dispersion, such as a molecular dispersion or partial molecular dispersion, in the substrate.

In embodiments of the invention, the third chemical compound may be chemically bound to the structure or internal surface (e.g. pores) of the substrate 2. For example, in case the third chemical compound is an ionic salt, the third chemical compound may be bound to a charged internal surface of the substrate. For example, the substrate may comprise cellulose fibres having a charged side group, such as for example carboxymethyl cellulose (CMC), wherein the third chemical compound may be bound to the cellulose fibres by ionic bonds.

The invention also relates to a method of manufacturing a medical dressing 30 comprising the steps of:
    providing an adhesive layer 3 comprising a first chemical compound; and
    providing a coating 9 comprising a second chemical compound on the adhesive layer 3.

In embodiments of the invention, the step of providing an adhesive layer 3 comprising a first chemical may include a step of adding a first chemical compound to an uncured adhesive mixture, such as for example an uncured mixture of a silicone based adhesive, and subsequently curing the adhesive mixture, to thereby achieve an adhesive layer 3 having the first chemical compound incorporated therewithin.

In embodiments of the invention, the step of providing a coating comprising a second chemical compound on the adhesive layer 3 may include adding the second chemical compound to the skin-facing surface 6 of the adhesive layer 3 in the form of a solid, e.g. a powder, alternatively, the second chemical compound may be dissolved or dispersed in a suitable solvent, e.g. water or organic solvents such as alcohol, thus a solution or suspension of the second chemical compound may be applied to the adhesive layer 3, in which case the method typically comprise a further step of drying, e.g. evaporating the liquid. In embodiments of the invention, a liquid mixture (e.g. solution or suspension) of the second chemical compound may further comprise a film forming or carrier chemical compound (as discussed above), thereby a film coating comprising the second chemical compound and the film forming chemical compound may be achieved. A liquid mixture (e.g. solution or suspension) of the second chemical compound may be applied by means of, for example, a sponge applicator, a brush, or a stick, or a roller, or by spreading with a spatula, or by release by a release sheet, or the liquid mixture may be in the form of a spray, mousse, aerosol, or foam which may be directly applied to the surface. For example, a liquid mixture (e.g. solution or suspension) of the second chemical compound may typically be applied to the adhesive layer 3 by spraying the liquid mixture on the skin-facing surface 6 of the adhesive layer 3. In embodiments of the invention, in case the second chemical compound is dissolved or dispersed in a solvent, the viscosity of the solvent may be configured to thereby control the level of penetration of the second chemical compound into the skin-facing surface 6 of adhesive layer 3. For example, the viscosity of a liquid mixture (e.g. solution or suspension) of the second chemical compound may typically have a relatively low viscosity, such as for example within the range of 0.65 to 500 mPas.

Where features, embodiments, or aspects of the present invention are described in terms of Markush groups, a person skilled in the art will recognize that the invention is also thereby described in terms of any individual member or subgroup of members of the Markush group. The person skilled in the art will further recognize that the invention is also thereby described in terms of any combination of individual members or subgroups of members of Markush groups.

Additionally, it should be noted that embodiments and features described in the context of one of the aspects and/or embodiments of the present invention also apply mutatis mutandis to all the other aspects and/or embodiments of the invention.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The advantages of the invention have been demonstrated in experiments.

EXAMPLES

Preparation of Example Embodiments of the Invention
Materials Used:

Wacker SilGel® 612 silicone based adhesive (room temperature vulcanization silicone; two component system) commercially available from Wacker; silver sulfate ($Ag_2SO_4$) commercially available from Alfa Aesar; CMC from Akzo Nobel, polyurethane film with a thickness of about 25 μm, commercially available from Epurex.

Example 1

43.3 g Silgel 612 part B was mixed thoroughly with 11.1 g CMC. After a homogenous mixture had been achieved, 45.6 g Silgel 612 part A was added and the blend was mixed thoroughly. The mixed silicone with about 11% CMC was coated on a polyurethane film at a coat weight of 60 gsm and cured at 145° C. for 5 minutes. After cooling, an aqueous solution of silver sulfate (7.0 g/L) was prepared and subsequently substantially uniformly sprayed (using any suitable coating apparatus or e.g. a spray can) on the cured silicone layer, and the sample was dried at room temperature for at least 24 h. The total amount sprayed was 16.4 4/cm² giving a total amount of silver sulfate on the silicone layer of about 115 μg/cm².

Example 2

42.4 g Silgel 612 part B was mixed thoroughly with 1.91 g silver sulfate and 11.1 g CMC. After a homogenous mixture had been achieved, 44.6 g Silgel 612 part A was added and the blend was mixed thoroughly. The mixed silicone with 1.91% silver sulfate and 11.1% CMC was coated on a polyurethane film at a coat weight of 60 gsm and cured at 145° C. for 5 minutes. The silver concentration of the silicone coated film was about 115 μg/cm².

Example 3

42.6 g Silgel 612 part B was mixed thoroughly with 1.59 g silver sulfate and 11.0 g CMC. After a homogenous mixture had been achieved, 44.8 g Silgel 612 part A was added and the blend was mixed thoroughly. The mixed silicone with 1.59% silver sulfate and 11% CMC was coated on a polyurethane film at a coat weight of 60 gsm and cured at 145° C. for 5 minutes. The silicone coated film received a silver concentration of about 95 μg/cm². After cooling, an aqueous solution of silver sulfate (2.67 g/L) was prepared and subsequently substantially uniformly sprayed (using any suitable coating apparatus or e.g. a spray can) on the cured silicone layer, and the sample was dried at room temperature for at least 24 h. The total amount sprayed was 7.5 μL/cm², giving a total amount of silver sulfate on the silicone layer of about 20 μg/cm², and thus a total amount of silver sulfate in the final product of about 115 μg/cm².

Silver Release Tests

The release of silver was determined by using a shaking method. In principle, the test material was submerged into a test medium for a specified period of time at a specified temperature. Thereafter, the test material was removed from the test medium and submerged into a another well with fresh test medium, and further incubated for a specific time period. This procedure was repeated for additional times. The silver concentration in the test medium exposed to the test material was determined by acid digestion followed by analysis by Inductively Couples Plasma Optic Emission Spectroscopy (ICP-OES).

Method Description

Circular pieces (Ø 28 mm) of Examples 1-3 were punched in triplicate and placed into separate wells of a 6-well plate containing 2 ml of 10% Nutrient Broth (NB) in water. The 6-well plates were incubated at 35° C.±2° C. and at 100 rpm±5 rpm for 2 hours. After incubation, the circular pieces of Examples 1-3 were moved to new wells of 6-well plates, containing fresh 10% NB. The new 6-well plates were incubated at 35° C.±2° C. and at 100 rpm±5 rpm for additional 4 hours (6 hours in total). This procedure was repeated additional two times with incubation periods of 18 h (24 hours in total) and 24 hours (48 hours in total), respectively.

The silver concentration was determined in the test suspension exposed to the punched pieces. The total volume of the test suspension in the wells (approximate 2 ml) was mixed with 30 ml hydrochloric acid (32%) and 6 ml of nitric acid (65%). The mixture was heated to 70° C. for 4 h and then allowed to cool. Thereafter, the solutions were transferred to 100 ml volumetric flasks and diluted. The silver concentrations in the volumetric flasks were thereafter analyzed with Inductively Coupled Plasma Optical Emission Spectroscopy (Thermo Fisher iCAP 6000 series) at the wavelengths 328.068 nm and 338.289 nm by using axial mode. Calibration range was 0.01-20 mg/L. Standards were prepared by adding silver stock solutions to blank sample matrix (10% NB). Standards were treated as samples. The results were reported as μg released silver per cm².

Results and Discussion

The released amounts of silver for Examples 1-3 for every measure point are presented in FIG. 2. The total amount of silver released at the end of the testing (48 hours) is presented in Table 1. Values are mean of three samples.

TABLE 1

| Sample | Total amount (μg Ag/cm²) | Relative amount (%) |
|---|---|---|
| Example 1 | 68.4 | 86.1 |
| Example 2 | 7.5 | 9.5 |
| Example 3 | 16.5 | 20.8 |

As illustrated in FIG. 2a, Example 1 ($Ag_2SO_4$ on surface) shows a very fast and high release, with 80% of total content being released already within the first 2 hours. However, already at 6 hours, the release decreases rapidly down to 5%, and thereafter, the release is at 1% of total content or below, because most of the silver has already been released and the material is depleted. A product like this has most probably an initial strong antimicrobial effect, but needs to be changed relatively often. There is also a risk that an initial uncontrolled release can cause toxic silver concentrations in the wound, and thereby delay the wound healing.

In contrast, Example 2 ($Ag_2SO_4$ incorporated in adhesive layer) releases only 4% of the total silver content within the first 2 hours, and thereafter, the release stays at a stable level of 2% at every sampling point thereafter. Significantly less silver is available when located in the silicone, compared to when it is present at the surface. After 48 hours of testing, only 10 percent of total silver in the material is released (see Table 1), i.e. most of the added silver is not of use. As silver is a relatively expensive chemical, it is of commercial interest that the major part of the added silver is of use, otherwise it is thrown away at the next dressing change. On the other hand, it is reasonable to assume that the release will continue at about the same level for additional time points. Hence, a product with those properties would lack an initial antimicrobial effect, would not be cost effective, but would exert antimicrobial activity for an extended time.

Example 3 is an example embodiment according to the invention, and comprises Ag$_2$SO$_4$ sprayed onto the surface, and incorporated in the silicone film. The total silver of Example 3 concentration is the same as for Example 1 and 2, i.e. 115 μg silver sulfate per cm$^2$ (80 μg Ag/cm$^2$). As illustrated in in FIG. 2, a different release profile is obtained as compared to Examples 1 and 2. After 2 hours, 16% of the total silver content has been released, and thereafter, the release stays at a range between 1-2% at every sampling point. At the end of the test, about 21% of the total silver amount has been released, which is significantly higher compared to Example 2. The silver on the surface is easily available and is responsible for a relatively high initial release, which in turn can boost an antimicrobial effect. The silver in the silicone is less available, but gives a stable contribution and provides for the sustained release over time. A product according to the invention would provide for an initial, efficient as well as sustained antimicrobial effect.

The invention claimed is:

1. A medical dressing comprising an adhesive layer having a skin-facing surface to adhere the medical dressing to a dermal surface, wherein said adhesive layer comprises a first chemical compound incorporated within said adhesive layer, and wherein at least a portion of said skin-facing surface comprises a coating comprising a second chemical compound being a silver salt.

2. The medical dressing according to claim 1, wherein said adhesive layer comprises a silicone based adhesive.

3. The medical dressing according to claim 1, wherein said medical dressing further comprises a substrate having a first surface facing said adhesive layer, wherein said skin-facing surface of said adhesive layer faces away from said first surface of said substrate.

4. The medical dressing according to claim 3, wherein said adhesive layer is a coating on at least a portion of said first surface of said substrate.

5. The medical dressing according to claim 3, wherein said medical dressing further comprises a perforated film layer sandwiched between said first surface of said substrate and said adhesive layer, wherein said adhesive layer is a coating on a non-perforated portion of said perforated film layer.

6. The medical dressing according to claim 3, wherein said substrate comprises an absorbent material.

7. The medical dressing according to claim 6, wherein said absorbent material is selected from the group consisting of a polymeric foam, a non-woven material, a fibrous material, a gel forming fiber, a hydrogel, a matrix containing hydrocolloids, a woven fiber, and a knitted fiber.

8. The medical dressing according to claim 3, wherein said substrate is a polymeric film.

9. The medical dressing according to claim 3, wherein said substrate comprises a third chemical compound, wherein said third chemical compound is the same as said first and/or second chemical compound.

10. The medical dressing according to claim 1, wherein said coating comprising said second chemical compound is intended to be in direct contact with a wound and/or surrounding dermal surface during use.

11. The medical dressing according to claim 1, wherein said first chemical compound and/or said second chemical compound is an antimicrobial compound.

12. The medical dressing according to claim 1, wherein said first chemical compound is selected from the group consisting of a silver compound, a biguanide salt, iodine, salicylic acid or any salt thereof, acetylsalicylic acid or any salt thereof, a quarter ammonium salt, povidone-iodine, lactoferrin, xylitol, an antimicrobial peptide, borneol, bismuth subgallate, an antifungal pharmaceutical, and an antibiotic.

13. The medical dressing according to claim 1, wherein said first chemical compound is present in a first concentration by area of said medical dressing and said second chemical compound is present in a second concentration by area of said medical dressing, wherein said first and second concentrations are different.

14. The medical dressing according to claim 1, wherein a concentration of said first chemical compound is about 5 to 3000 μg/cm$^2$, and wherein a concentration of said second chemical compound is about 1 to 2500 μg/cm$^2$.

15. A method of manufacturing the medical dressing of claim 1 comprising the steps of:
providing an adhesive layer comprising the first chemical compound; and
providing a coating comprising the second chemical compound on said adhesive layer.

* * * * *